US005576269A

United States Patent [19]
Hirabayashi et al.

[11] Patent Number: 5,576,269
[45] Date of Patent: Nov. 19, 1996

[54] HERBICIDAL COMPOSITION COMPRISING OXADIAZOLO- OR THIADIAZOLO-[3,4A]-PYRIDAZINE DERIVATIVES, AN N-ALKYLPYRROLIDONE, AND ORGANIC SOLVENT

[75] Inventors: Yoshinori Hirabayashi, Shizuoka; Shigeki Fujita, Yaizu; Kanji Nakamura; Susumu Kato, both of Shizuoka, all of Japan

[73] Assignee: Kumiai Chemical Industry Co., Ltd., Tokyo, Japan

[21] Appl. No.: 514,519

[22] Filed: Aug. 11, 1995

Related U.S. Application Data

[63] Continuation of Ser. No. 185,965, filed as PCT/JP93/0095, Jul. 10, 1992, abandoned.

[30] Foreign Application Priority Data

Jul. 10, 1992 [JP] Japan ................................ 4-206216

[51] Int. Cl.⁶ .................................................. A01N 43/90
[52] U.S. Cl. ............................................................ 504/236
[58] Field of Search .............................................. 504/236

[56] References Cited

U.S. PATENT DOCUMENTS 5,039,331  8/1991  Satow et al. ................................ 71/90
5,071,463  12/1991  Narayanan et al. ........................ 71/79

*Primary Examiner*—S. Mark Clardy
*Attorney, Agent, or Firm*—Oblon, Spivak, McClelland, Maier & Neustadt, P.C.

[57] ABSTRACT

A composition comprising a condensed heterocyclic derivative and an N-alkyl-2-pyrrolidone and another organic solvent for enhanced stability. Particularly high effects can be obtained with a composition wherein the ratio of the condensed heterocyclic derivative to the N-alkyl-2-pyrrolidone is within a range of from 2:1 to 1:1000.

15 Claims, No Drawings

HERBICIDAL COMPOSITION COMPRISING OXADIAZOLO- OR THIADIAZOLO-[3,4A]-PYRIDAZINE DERIVATIVES, AN N-ALKYLPYRROLIDONE, AND ORGANIC SOLVENT

This is a continuation of application Ser. No. 08/185,965 filed on Feb. 8, 1994 now abandoned, which was filed as International Application PCT/JP93/00955 on Jul. 10, 1992.

TECHNICAL FIELD

The present invention relates to a herbicidal composition comprising a condensed heterocyclic derivative and an N-alkyl-2-pyrrolidone, which has high herbicidal effects and whereby the stability of the active ingredient is excellent.

BACKGROUND ART

Condensed heterocyclic derivatives to be used in the present invention (hereinafter referred to as condensed heterocyclic derivatives) are compounds disclosed in e.g. Japanese Unexamined Patent Publications No. 264489/1988, No. 76487/1986, No. 250388/1989 and No. 289573/1990. These compounds are known to have high herbicidal activities against weeds in upland fields and paddy fields and high selectivity for crop plants such as soy bean and corn. When such condensed heterocyclic derivatives are to, be used as herbicides at upland fields or paddy fields, they are formulated into wettable powders or suitable formulations such as granular wettable powders, emulsifierable concentrates or flowables, which will be diluted with water for application.

Generally, an agricultural chemical is desired to be highly active at a low dose, and various methods have been studied for improving the activities of agricultural chemicals. For example, a composition containing a product obtained by co-pulverization of an agricultural chemical compound and a water-soluble polymer compound (Japanese Unexamined Patent Publication No. 308202/1989) and a composition containing a residue obtained by distilling a solvent off from a solution having an agricultural chemical compound and a water-soluble polymer compound dissolved in inorganic solvent (Japanese Unexamined Patent Publication No. 211504/1989) have been disclosed.

At the time of applying a herbicide, an excess amount of the active agent is applied in many cases to obtain adequate effects. However, it is undesirable to apply a large amount of the active agent from the viewpoint of the economical burden on farmers or possible dangers to the safety to human and animals and environmental pollution. An agricultural chemical composition is desired which is free from phytotoxicity to crop plants and which is capable of providing adequate effects in a less amount of the active agent used.

If the above-mentioned water-soluble compound is incorporated for the purpose of improving the herbicidal effects of a thiadiazabicyclononane derivative, it is likely that during the storage, the thiadiazabicyclononane derivative undergoes decomposition, whereby not only it is impossible to obtain the herbicidal effects of the original compound, but also phytotoxicity to crop plants may result in some cases.

DISCLOSURE OF INVENTION

As a result of an earnest research with an object to improve the herbicidal effects of the condensed heterocyclic derivatives, the present inventors have found it possible to obtain a herbicidal composition having high herbicidal effects and being durable for storage for a long period of time by incorporating an N-alkyl-2-pyrrolidone to the condensed heterocyclic derivatives.

The herbicidal composition of the present invention comprises a condensed heterocyclic derivative and an N-alkyl-2-pyrrolidone.

The condensed heterocyclic derivative as an active ingredient of the herbicidal composition of the present invention is a solid or liquid compound of the formula:

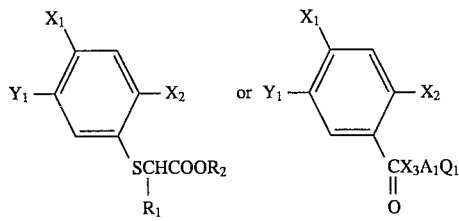

wherein each of $X_1$ and $X_2$ is a hydrogen atom or a halogen atom, $R_1$ is a hydrogen atom or an alkyl group, $R_2$ is a hydrogen atom, an alkyl group, a cycloalkyl group or an alkoxyalkyl group, $X_3$ is an oxygen atom or a sulfur atom, $A_1$ is a linear or branched alkylene group, $Q_1$ is a phenyl group, a halogen-substituted phenyl group, a cycloalkoxycarbonyl group, an alkylthio group, an alkoxycarbonyl group, an alkoxyalkoxycarbonyl group, an alkoxycarbonylalkylthio group or an alkylthioalkoxycarbonyl group, and $Y_1$ is a group of the formula:

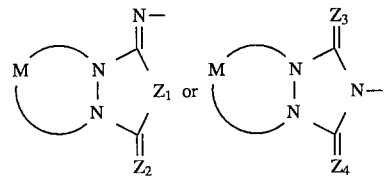

wherein each of $Z_1$, $Z_2$, $Z_3$ and $Z_4$ is an oxygen atom or a sulfur atom, and M is a $C_4$ alkylene group or a $C_4$ alkenylene group.

Referred is a condensed heterocyclic derivative of the formula:

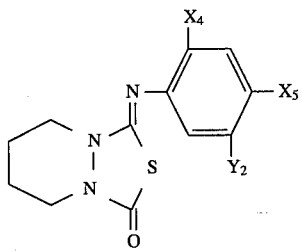

wherein each of $X_4$ and $X_5$ is a hydrogen atom or a halogen atom, $Y_2$ is a group of the formula

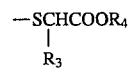

(wherein $R_3$ is a hydrogen atom or an alkyl group, and $R_4$ is an alkyl group, a cycloalkyl group or an alkoxyalkyl $$-\overset{\overset{\text{O}}{\|}}{\text{C}}\text{X}_6\text{A}_2\text{Q}_2$$

group) or a group of the formula
(wherein $X_6$ is an oxygen atom or a sulfur atom, $A_2$ is a linear or branched alkylene group, and $Q_2$ is a phenyl group, a halogen-substituted phenyl group, a cycloalkoxycarbonyl group, an alkylthio group, an alkoxycarbonyl group, an alkoxyalkoxycarbonyl group, an alkoxycarbonylalkylthio group or an alkylthioalkoxycarbonyl group).

Specific examples of the condensed heterocyclic derivatives are shown in Tables 1 to 12, but useful derivatives are not limited to such specific examples. Compound Nos. will be referred to in the subsequent description.

TABLE 1

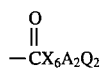

| Comp. No. | $X_4$ | $X_5$ | $Y_2$ |
|---|---|---|---|
| 1 | F | Cl | SCH$_2$COOC$_2$H$_5$ |
| 2 | F | Cl | SCHCOOC$_2$H$_5$<br>\|<br>C$_2$H$_5$ |
| 3 | F | Cl | SCHCOO—⬠H<br>\|<br>C$_2$H$_5$ |
| 4 | F | Cl | SCHCOOC$_2$H$_5$<br>\|<br>C$_3$H$_7$ |
| 5 | F | Cl | SCH$_2$COO—⬠H |
| 6 | F | Cl | SCHCOOCH$_2$CH$_2$OCH$_3$<br>\|<br>CH$_3$ |
| 7 | H | Cl | SCH$_2$COOC$_2$H$_5$ |
| 8 | H | Cl | SCH$_2$COO—⬠H |
| 9 | H | Cl | SCHCOOCH$_2$CH$_2$OCH$_3$<br>\|<br>CH$_3$ |
| 10 | H | Cl | SCHCOOC$_2$H$_5$<br>\|<br>C$_2$H$_5$ |
| 11 | H | Cl | SCHCOO—⬠H<br>\|<br>C$_2$H$_5$ |

TABLE 2

| Comp. No. | $X_4$ | $X_5$ | $Y_2$ |
|---|---|---|---|
| 12 | H | Cl | SCHCOOC$_2$H$_5$<br>\|<br>C$_4$H$_9$ |
| 13 | H | Cl | SCHCOOC$_2$H$_5$<br>\|<br>C$_3$H$_7$ |
| 14 | H | Cl | SCHCOOC$_3$H$_7$<br>\|<br>C$_3$H$_7$ |
| 15 | H | Cl | SCHCOO—⬠H<br>\|<br>C$_3$H$_7$ |
| 16 | H | Cl | SCHCOOCH$_3$<br>\|<br>C$_3$H$_7$ |
| 17 | F | Cl | SCHCOOC$_3$H$_7$<br>\|<br>C$_2$H$_5$ |
| 18 | F | Cl | SCHCOOCH$_3$<br>\|<br>C$_3$H$_7$ |
| 19 | F | Cl | SCHCOOC$_3$H$_7$<br>\|<br>C$_3$H$_7$ |
| 20 | F | Cl | SCHCOO—⬠H<br>\|<br>C$_3$H$_7$ |
| 21 | F | Cl | SCHCOOC$_2$H$_5$<br>\|<br>C$_4$H$_9$ |
| 22 | H | Cl | SCH$_2$COOCH$_3$ |
| 23 | F | Cl | SCH$_2$COOCH$_3$ |
| 24 | H | Cl | SCHCOOCH$_3$<br>\|<br>C$_2$H$_5$ |
| 25 | H | Cl | SCHCOOCH$_3$<br>\|<br>C$_4$H$_9$ |
| 26 | H | Cl | SCHCOOC$_2$H$_5$<br>\|<br>C$_3$H$_7$-i |
| 27 | H | Cl | SCHCOOC$_2$H$_5$<br>\|<br>C$_4$H$_9$-s |

TABLE 3

| Comp. No. | $X_4$ | $X_5$ | $Y_2$ |
|---|---|---|---|
| 28 | H | Cl | SCHCOOC$_2$H$_5$<br>\|<br>C$_4$H$_9$-i |
| 29 | H | Cl | SCH$_2$COOC$_3$H$_7$ |
| 30 | F | Cl | SCH$_2$COOC$_3$H$_7$ |
| 31 | H | Cl | SCHCOOC$_3$H$_7$<br>\|<br>C$_2$H$_5$ |

TABLE 3-continued

| Comp. No. | $X_4$ | $X_5$ | $Y_2$ |
| --- | --- | --- | --- |
| 32 | H | Cl | SCHCOOC$_3$H$_7$<br>\|<br>C$_4$H$_9$ |
| 33 | H | Cl | SCH$_2$COOC$_3$H$_7$-i |
| 34 | F | Cl | SCH$_2$COOC$_3$H$_7$-i |
| 35 | H | Cl | SCHCOOC$_3$H$_7$-i<br>\|<br>C$_2$H$_5$ |
| 36 | H | Cl | SCHCOOC$_3$H$_7$-i<br>\|<br>C$_3$H$_7$ |
| 37 | H | Cl | SCHCOOC$_3$H$_7$-i<br>\|<br>C$_4$H$_9$ |
| 38 | H | Cl | SCH$_2$COOC$_4$H$_9$ |
| 39 | F | Cl | SCH$_2$COOC$_4$H$_9$ |
| 40 | H | Cl | SCHCOOC$_4$H$_9$<br>\|<br>C$_2$H$_5$ |
| 41 | H | Cl | SCHCOOC$_4$H$_9$<br>\|<br>C$_3$H$_7$ |
| 42 | H | Cl | SCHCOOC$_4$H$_9$<br>\|<br>C$_4$H$_9$ |
| 43 | H | Cl | SCH$_2$COOC$_4$H$_9$-s |
| 44 | F | Cl | SCH$_2$COOC$_4$H$_9$-s |

TABLE 4

| Comp. No. | $X_4$ | $X_5$ | $Y_2$ |
| --- | --- | --- | --- |
| 45 | H | Cl | SCHCOOC$_4$H$_9$-s<br>\|<br>C$_2$H$_5$ |
| 46 | H | Cl | SCHCOOC$_4$H$_9$-s<br>\|<br>C$_3$H$_7$ |
| 47 | H | Cl | SCHCOOC$_4$H$_9$-s<br>\|<br>C$_4$H$_9$ |
| 48 | H | Cl | SCH$_2$COOC$_4$H$_9$-i |
| 49 | F | Cl | SCH$_2$COOC$_4$H$_9$-i |
| 50 | H | Cl | SCHCOOC$_4$H$_9$-i<br>\|<br>C$_2$H$_5$ |
| 51 | H | Cl | SCHCOOC$_4$H$_9$-i<br>\|<br>C$_3$H$_7$ |
| 52 | H | Cl | SCHCOOC$_4$H$_9$-i<br>\|<br>C$_4$H$_9$ |
| 53 | H | Cl | SCH$_2$COOC$_5$H$_{11}$ |
| 54 | F | Cl | SCH$_2$COOC$_5$H$_{11}$ |
| 55 | H | Cl | SCHCOOC$_5$H$_{11}$<br>\|<br>C$_2$H$_5$ |

TABLE 4-continued

| Comp. No. | $X_4$ | $X_5$ | $Y_2$ |
| --- | --- | --- | --- |
| 56 | H | Cl | SCHCOOC$_5$H$_{11}$<br>\|<br>C$_3$H$_7$ |
| 57 | H | Cl | SCHCOOC$_5$H$_{11}$<br>\|<br>C$_4$H$_9$ |
| 58 | H | Cl | SCH$_2$COOC$_5$H$_{11}$-i |
| 59 | F | Cl | SCH$_2$COOC$_5$H$_{11}$-i |
| 60 | H | Cl | SCH$_2$COOC$_6$H$_{13}$ |

TABLE 5

| Comp. No. | $X_4$ | $X_5$ | $Y_2$ |
| --- | --- | --- | --- |
| 61 | F | Cl | SCH$_2$COOC$_6$H$_{13}$ |
| 62 | H | Cl | SCH$_2$COO—⟨C$_6$H$_{11}$⟩ |
| 63 | F | Cl | SCH$_2$COO—⟨C$_6$H$_{11}$⟩ |
| 64 | H | Cl | SCHCOO—⟨C$_6$H$_{11}$⟩<br>\|<br>C$_3$H$_7$ |
| 65 | H | Cl | SCH$_2$COOCH$_2$CH$_2$OCH$_3$ |
| 66 | F | Cl | SCH$_2$COOCH$_2$CH$_2$OCH$_3$ |
| 67 | H | Cl | SCHCOOCH$_2$CH$_2$OCH$_3$<br>\|<br>C$_3$H$_7$ |
| 68 | H | Cl | SCH$_2$COOC$_5$H$_{11}$-s |
| 69 | F | Cl | SCH$_2$COOC$_5$H$_{11}$-s |
| 70 | H | Cl | SCH$_2$COOCH$_2$CHC$_2$H$_5$<br>\|<br>CH$_3$ |
| 71 | H | Cl | SCH$_2$COOCH$_2$CHC$_2$H$_5$<br>\|<br>CH$_3$ |
| 72 | H | Cl | SCH$_2$COOCH$_2$CH$_2$OC$_2$H$_5$ |
| 73 | F | Cl | SCH$_2$COOCH$_2$CH$_2$OC$_2$H$_5$ |
| 74 | H | Cl | SCH$_2$COOCH$_2$C$_4$H$_9$-t |
| 75 | F | Cl | SCH$_2$COOCH$_2$C$_4$H$_9$-t |
| 76 | H | Cl | SCH$_2$COOCH$_2$CH$_2$OC$_3$H$_7$-i |

TABLE 6

| Comp. No. | $X_4$ | $X_5$ | $Y_2$ |
| --- | --- | --- | --- |
| 77 | F | Cl | SCH$_2$COOCH$_2$CH$_2$OC$_3$H$_7$-i |
| 78 | H | Cl | SCH$_2$COOCH$_2$CH$_2$OC$_4$H$_9$ |
| 79 | F | Cl | SCH$_2$COOCH$_2$CH$_2$OC$_4$H$_9$ |

TABLE 7

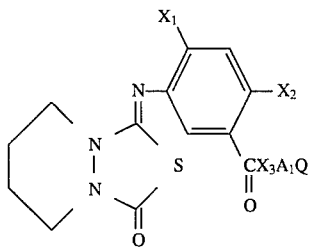

| Comp. No. | $X_1$ | $X_2$ | $X_3$ | $A_1$ | $Q_1$ |
|---|---|---|---|---|---|
| 80 | F | Cl | O | $CH_2$ | $COOC_2H_4SCH_3$ |
| 81 | F | Cl | O | CH(CH_3) | $COOC_2H_4SCH_3$ |
| 82 | F | Cl | S | $CH_2$ | $COOCH(CH_3)CH_2OCH_3$ |
| 83 | F | Cl | S | $CH_2$ | $COOC_2H_4OC_2H_5$ |
| 84 | F | Cl | S | CH(CH_3) | $COOC_2H_4OCH_3$ |
| 85 | F | Cl | S | CH(CH_3) | $COOC_2H_4OC_2H_5$ |
| 86 | F | Cl | S | CH(CH_3) | $COOCH(CH_3)CH_2OCH_3$ |
| 87 | F | Cl | O | $CH_2$ | $COOCH_3$ |
| 88 | F | Cl | O | $CH_2$ | $COOC_5H_{11}$ |
| 89 | F | Cl | O | CH(CH_3) | $COOCH_3$ |
| 90 | F | Cl | O | CH(CH_3) | $COOC_2H_5$ |
| 91 | F | Cl | O | CH(CH_3) | $COOC_3H_7$ |

TABLE 8

| Comp. No. | $X_1$ | $X_2$ | $X_3$ | $A_1$ | $Q_1$ |
|---|---|---|---|---|---|
| 92 | F | Cl | O | CH(CH_3) | $COOC_3H_7$-i |
| 93 | F | Cl | O | CH(CH_3) | $COOC_4H_9$ |
| 94 | F | Cl | O | CH(CH_3) | $COOC_4H_9$-i |
| 95 | F | Cl | O | CH(CH_3) | $COOC_4H_9$-s |
| 96 | F | Cl | S | $CH_2$ | $COOCH_3$ |
| 97 | F | Cl | S | $CH_2$ | $COOC_2H_5$ |
| 98 | F | Cl | O | $CH_2CH_2$ | $SCH_3$ |
| 99 | F | Cl | O | $CHCH_2$(CH_3) | $SCH_3$ |
| 100 | F | Cl | O | $CHCH_2$(CH_3) | $SC_2H_5$ |
| 101 | F | Cl | O | $CHCH_2$(CH_3) | $SC_3H_7$ |
| 102 | F | Cl | O | $CHCH_2$(CH_3) | $SC_3H_7$-i |
| 103 | F | Cl | O | $CHCH_2$(CH_3) | $SC_4H_9$ |
| 104 | F | Cl | O | $CHCH_2$(CH_3) | $SC_4H_9$-s |
| 105 | F | Cl | O | $CHCH_2$(CH_3) | $SC_5H_{11}$ |
| 106 | F | Cl | O | $CHCH_2$(CH_3) | $SC_6H_{13}$ |
| 107 | F | Cl | O | $CH_2CH_2$ | phenyl |
| 108 | F | Cl | O | $CHCH_2$(CH_3) | $SCH_2COOC_2H_5$ |

TABLE 9

| Comp. No. | $X_1$ | $X_2$ | $X_3$ | $A_1$ | $Q_1$ |
|---|---|---|---|---|---|
| 109 | F | Cl | O | $CH_2$ | COO-C$_6$H$_{11}$ |
| 110 | F | Cl | O | CH(CH_3) | COO-C$_6$H$_{11}$ |
| 111 | F | Cl | S | $CH_2$ | COO-C$_6$H$_{11}$ |
| 112 | F | Cl | O | $CH_2$ | $COOC_2H_5$ |
| 113 | F | Cl | O | $CH_2$ | $COOC_2H_4OCH_3$ |
| 114 | F | Cl | O | CH(CH_3) | $COOC_2H_4OCH_3$ |
| 115 | F | Cl | S | $CH_2$ | $COOC_2H_4OCH_3$ |
| 116 | F | Cl | S | $CH_2$ | $COOC_3H_7$ |
| 117 | F | Cl | S | $CH_2$ | $COOC_3H_7$-i |
| 118 | F | Cl | S | $CH_2$ | $COOC_4H_9$ |
| 119 | F | Cl | S | $CH_2$ | $COOC_4H_9$-s |
| 120 | F | Cl | S | $CH_2$ | $COOC_4H_9$-i |
| 121 | F | Cl | S | $CH_2$ | $COOC_4H_9$-t |
| 122 | F | Cl | S | CH(CH_3) | $COOCH_3$ |

TABLE 9-continued

| Comp. No. | X₁ | X₂ | X₃ | A₁ | Q₁ |
|---|---|---|---|---|---|
| 123 | F | Cl | S | CH(CH₃) | COOC₂H₅ |
| 124 | F | Cl | S | CH(CH₃) | COOC₃H₇ |
| 125 | F | Cl | S | CH(CH₃) | COOC₃H₇ |

TABLE 10

| Comp. No. | X₁ | X₂ | X₃ | A₁ | Q₁ |
|---|---|---|---|---|---|
| 126 | F | Cl | S | CH(CH₃) | COOC₄H₉ |
| 127 | F | Cl | S | CH(CH₃) | COOC₄H₉-s |
| 128 | F | Cl | S | CH(CH₃) | COOC₄H₉-i |
| 129 | F | Cl | O | CHCH₂(CH₃) | —C₆H₅ |
| 130 | F | Cl | O | CHCH₂(CH₃) | —C₆H₄—Cl |

TABLE 11

| Comp. No. | X₄ | X₆ | Y₂ |
|---|---|---|---|
| 131 | Cl | F | SCH₂COOCH₃ |
| 132 | Cl | F | SCHCOOCH₃ (CH₃) |
| 133 | Cl | F | SCHCOOC₂H₅ (C₂H₅) |
| 134 | Cl | F | SCHCOOC₄H₉ (CH₃) |
| 135 | Cl | Cl | SCH₂COOC₂H₅ |

TABLE 12

| Comp. No. |
|---|
| 136  |

TABLE 12-continued

| Comp. No. |
|---|
| 137 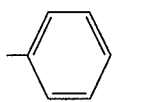 |
| 138 |

The N-alkyl-2-pyrrolidone to be used in the present invention, is a water-soluble or water-insoluble compound which is liquid at room temperature. The carbon number of the alkyl of the N-alkyl-2-pyrrolidone to be used in the present invention, is preferably within a range of from 1 to 12, and the alkyl may be linear or branched. Typical compounds include, for example, N-methyl-2-pyrrolidone, N-octyl-2-pyrrolidone and N-dodecyl-2-pyrrolidone. Among them, N-methyl-2-pyrrolidone is most suitable. They are water-soluble or water-insoluble compounds which are liquid at room temperature. For N-octyl-2-pyrrolidone and N-dodecyl-2-pyrrolidone, a linear alkyl group is preferred. N-alkyl-2-pyrrolidones may be used alone or in combination as a mixture of two or more of them.

The condensed heterocyclic derivative and the N-alkyl-2-pyrrolidone used in the present invention, are mixed in a weight ratio of from 2:1 to 1:1000, preferably from 1:1 to 1:100.

Further, the blend proportion of the condensed heterocyclic derivative and the N-alkyl-2-pyrrolidone in the composition is from 0.1 wt % to 99 wt %.

To prepare the herbicidal composition of the present invention, the condensed heterocyclic derivative may usually be preliminarily dissolved in the N-alkyl-2-pyrrolidone, and then, other raw materials may be blended to obtain the herbicidal composition. However, it is not necessarily required to preliminarily dissolve the condensed heterocyclic derivative in the N-alkyl-2-pyrrolidone, and the condensed heterocyclic derivative and the N-alkyl-2-pyrrolidone may be blended separately.

The herbicidal composition of the present invention may be formed into a solid formulation such as a wettable powder or a granular wettable powder or into a liquid formulation such as an emulsifierable concentrate or a flowable dispersed in water. In such a case, a surfactant, a bulking agent, an organic solvent, a binder, a thickener and other adjuvants which are commonly employed for agricultural chemical formulations, may be employed, as the case requires. The surfactant may, for example, be an anionic or nonionic surfactant such as an alkyl phosphate, a polyoxyethylene alkyl ether, a polyoxyethylene alkylaryl ether, a polyalkylene glycol, a block polymer of polyoxyethylene-polyoxypropylene, an alkylaryl sulfate, a polyoxyethylene alkylaryl ether sulfate, a polyoxyethylene alkylaryl ether sulfate, a lignin sulfonate, naphthalene sulfonate or a dialkyl sulfosuccinate. The bulking agent may, for example, be a fine mineral powder such as clay, talc, diatomaceous earth, calcium carbonate or bentonite, a saccharide such as lactose or sugar, a water-soluble bulking agent such as urea, ammonium sulfate or sodium sulfate, fine silica powder, or water. The organic solvent may, for example, be a glycol such as ethylene glycol, propylene glycol or polyethylene glycol, an alcohol such as methanol, n-propyl alcohol, isopropyl alcohol or isostearyl alcohol, a vegetable oil such as soybean oil or rapeseed oil, a mineral oil such as kerosene, spindle oil or liquid paraffin, an aromatic hydrocarbon such as xylene, methylnaphthalene or phenylxylethane, a fatty acid such as oleic acid or isostearic acid, an ester such as tributyl phosphate, dioctyl phthalate, dimethyl glutarate, dimethyl succinate, a phthalic acid ester, a gluthalic acid ester or a succinic acid ester, or a solvent such as dimethyl sulfoxide or dimethyl formamide. The binder or thickener may, for example, be α-starch, carboxymethylcellulose, PVP, or xanthum gum. Other adjuvants may, for example, be silicon, a metal salt of a higher fatty acid or a coloring agent, but it is not limited to such specific examples.

Further, it is also possible to incorporate a herbicide component other than the condensed heterocyclic derivative to obtain a mixture formulation.

To formulate a wettable powder, for example, a solution having the condensed heterocyclic derivative preliminarily dissolved in the N-alkyl-2-pyrrolidone, is mixed with fine silica powder, and then the mixture is uniformly mixed with a surfactant and a bulking agent such as clay, talc, diatomaceous earth, calcium carbonate or bentonite. If necessary, the mixture is pulverized to fine powder. Otherwise, a mixture having the N-alkyl-2-pyrrolidone and fine silica powder preliminarily mixed, is uniformly mixed with the condensed heterocyclic derivative, the surfactant and the bulking agent, and if necessary, the mixture is pulverized to fine powder. When an organic solvent is used, as the case requires, it is incorporated usually by dissolving it in the N-alkyl-2-pyrrolidone.

To formulate a granular wettable powder, for example, a solution having the condensed heterocyclic derivative preliminarily dissolved in the N-alkyl-2-pyrrolidone, is mixed with fine silica powder, and then a surfactant, a binder and a bulking agent are mixed thereto, and the mixture is stirred and mixed while adding a small amount of water, for granulation, followed by drying. Otherwise, a mixture having the N-alkyl-2-pyrrolidone and fine silica powder preliminarily mixed, is mixed with the condensed heterocyclic derivative, a surfactant, a binder and a bulking agent, and the mixture is stirred and mixed while adding a small amount of water, for granulation, followed by drying.

To formulate an emulsifiable concentrate, for example, the condensed heterocyclic derivative, the N-alkyl-2-pyrrolidone, a surfactant and an organic solvent are mixed and dissolved.

To formulate a flowable, for example, the condensed heterocyclic derivative, the N-alkyl-2-pyrrolidone, a surfactant, a thickener, an organic solvent, water and other adjuvants are mixed, and if necessary, pulverized.

The herbicidal composition comprising the condensed heterocyclic derivative and the N-alkyl-2-pyrrolidone, of the present invention, has a feature that the stability of the constituting components during the storage is very high, and it is free from deterioration of the herbicidal effects due to decomposition of the active ingredient or from formation of decomposed products which promote phytotoxicity. Accordingly, it is safe to crop plants even after being stored for a long period of time. Besides, high herbicidal effects can be obtained at a low dose, whereby it is unnecessary to apply the active agent in an excess amount, and thus it is free from a problem such as environmental pollution or danger to the safety of human and animals.

BEST MODE FOR CARRYING OUT THE INVENTION

Now, the present invention will be described in detail with reference to Examples and Test Examples. However, the present invention is by no means restricted to such Examples. In each Example, "parts" means "parts by weight".

EXAMPLE 1

Five parts of compound 1 and 20 parts of N-methyl-2-pyrrolidone were mixed and dissolved, and the solution was mixed with 30 parts of fine silica powder (trade name: Carplex #80, manufactured by Shionogi Pharmaceutical Co. Ltd.). Further, 5 parts of a polyoxyethylene alkylaryl ether sulfate (Trade name: Dikssol WK, manufactured by Daiichi Kogyoseiyaku) and 40 parts of clay were uniformly mixed thereto, followed by pulverization to obtain a wettable powder.

EXAMPLE 2

Five parts of compound 1, 15 parts of N-n-octyl-2-pyrrolidone and 15 parts of methylnaphthalene were mixed and dissolved, and the solution was mixed with 30 parts of fine silica powder (trade name: Carplex #80, manufactured by Shionogi Pharmaceutical Co. Ltd.). Further, 5 parts of a polyoxyethlene alkylaryl ether sulfate (trade name: Dikssol WK, manufactured by Daiichi Kogyoseiyaku) and 30 parts of clay were uniformly mixed thereto, followed by pulverization to obtain a wettable powder.

EXAMPLE 3

Five parts of compound 1, 15 parts of N-methyl-2-pyrrolidone, 7.5 parts of dimethyl glutarate and 7.5 parts of dimethyl succinate were mixed and dissolved, and the solution was mixed with 30 parts of fine silica powder (trade name: Carplex #67, manufactured by Shionogi Pharmaceutical Co. Ltd.). Further, 5 parts of a polyoxyethlenealkylether sulfate (trade name: Dikssol WK, manufactured by Daiichi Kogyoseiyaku) and 30 parts of clay were uniformly mixed thereto, followed by pulverization to obtain a wettable powder.

EXAMPLE 4

One part of compound 1, 50 parts of N-methyl-2-pyrrolidone, 29 parts of methylnaphthalene and 20 parts of a polyoxyethylene alkylaryl ether (trade name: Sorpol T-10, manufactured by Toho Chemical Co. Ltd.) were mixed and dissolved to obtain an emulsifiable concentrate.

EXAMPLE 5

Five parts of compound 1, 10 parts of N-n-dodecyl-2-pyrrolidone, 5 parts of a polyoxyethylene alkylaryl ether sulfate (trade name: Agrisol W-150S, manufacture by Kao), 12 parts of ethylene glycol, 0.1 part of xanthum gum and 67.9 parts of water were uniformly mixed, followed by pulverization to obtain a flowable.

EXAMPLE 6

Twenty parts of N-methyl-2-pyrrolidone was mixed with 30 parts of fine silica carbon (trade name: Carplex #80, manufactured by Shionogi Pharmaceutical Co. Ltd.), and 5 parts of compound 10, 5 parts of a polyoxyethylene alkylaryl ether sulfate (trade name: Dikssol WK, manufactured by Daiichi Kogyoseiyaku) and 40 parts of clay were uniformly mixed thereto, followed pulverization to obtain a wettable powder.

EXAMPLE 7

Five parts of N-n-octyl-2-pyrrolidone was mixed with 30 parts of fine silica powder (trade name: Carplex #80, manufactured by Shionogi Pharmaceutical Co. Ltd.). Further, 5 parts of compound 23, 5 parts of polyoxyethylene alkylaryl ether sulfate (trade name: Dikssol WK, manufactured by Daiichi Kogyoseiyaku) and 55 parts of clay were uniformly mixed thereto, followed pulverization to obtain a wettable powder.

EXAMPLE 8

Five parts of compound 90 and 20 parts of N-n-octyl2-pyrrolidone were mixed and dissolved, and the solution was mixed with 30 parts of fine silica powder (trade name: Carplex #80, manufactured by Shionogi Pharmaceutical Co. Ltd.). Further, 5 parts of a polyoxyethylene alkylaryl ether sulfate (trade name: Dikssol WK, manufactured by Daiichi Kogyoseiyaku) and 40 parts of clay were uniformly mixed thereto, followed pulverization to obtain a wettable powder.

EXAMPLE 9

0.2 part of compound 96 and 20 parts of N-methyl-2-pyrrolidone were mixed, and the solution was mixed with 30 parts of fine silica powder (trade name: Carplex #80, manufactured by Shionogi Pharmaceutical Co. Ltd.). Further, 5 parts of polyoxyethylene alkylaryl ether sulfate (trade name: Dikssol WK, manufactured by Daiichi Kogyoseiyaku) and 44.8 parts of clay were uniformly mixed, followed by pulverization to obtain a wettable powder.

EXAMPLE 10

Twenty parts of N-methyl-2-pyrrolidone and 30 parts of fine silica powder (trade name: Carplex #80, manufactured by Shionogi Pharmaceutical Co. Ltd.) were mixed, and 5 parts of compound 135, 5 parts of a polyoxyethylene alkylaryl ether sulfate (trade name: Dikssol WK, manufactured by Daiichi Kogyoseiyaku) and 40 parts of clay were uniformly mixed, followed by pulverization to obtain a wettable powder.

EXAMPLE 11

Five parts of compound 137 and 20 parts of N-n-dodecyl-2-pyrrolidone were mixed and dissolved, and the solution was mixed with 30 parts of fine silica powder (trade name: Carplex #80, manufactured by Shionogi Pharmaceutical Co. Ltd.). Further, 5 parts of a polyoxyethylenealkylarylether sulfate (trade name: Dikssol WK, manufactured by Daiichi Kogyoseiyaku) and 40 parts of clay were uniformly mixed, followed by pulverization to obtain a wettable powder.

EXAMPLE 12

Five parts of compound 138 and 20 parts of N-methyl-2-pyrrolidone were mixed and dissolved, and the solution was mixed with 30 parts of fine silica powder (trade name: Carplex #80, manufactured by Shionogi Pharmaceutical Co. Ltd.). Further, 5 parts of a polyoxyethylene alkylaryl ether sulfate (trade name: Dikssol WK, manufactured by Daiichi Kogyoseiyaku) and 40 parts of clay uniformly mixed thereto, followed by pulverization to obtain a wettable powder.

COMPARATIVE EXAMPLE 1

Five parts of compound 1, 30 parts of fine silica powder (trade name: Carplex #80, manufactured by Shionogi Pharmaceutical Co. Ltd.), 5 parts of a polyoxyethylene alkylaryl ether sulfate (trade name: Dikssol WK, manufactured by Daiichi Kogyoseiyaku) and 60 parts of clay were uniformly mixed followed by pulverization to obtain a wettable powder.

COMPARATIVE EXAMPLE 2

Five parts of compound 1, 5 parts of fine silica powder (trade name: Carplex #80, manufactured by Shionogi Pharmaceutical Co. Ltd.), 5 parts of a polyoxyethylene alkylaryl ether sulfate (trade name: Dikssol WK, manufactured by Daiichi Kogyoseiyaku) and 85 parts of clay were uniformly mixed, followed by pulverization to obtain a wettable powder.

COMPARATIVE EXAMPLE 3

Two parts of compound 1 and 40 parts of methylnaphthalene were mixed and dissolved, and the solution was mixed with 30 parts of fine silica powder (trade name: Carplex #80, manufactured by Shionogi Pharmaceutical Co. Ltd.). Further, 5 parts of a polyoxyethylene alkylaryl ether sulfate (trade name: Dikssol WK, manufactured by Daiichi Kogyoseiyaku) and 23 parts of clay were uniformly mixed thereto, followed by pulverization to obtain a wettable powder.

COMPARATIVE EXAMPLE 4

Twenty parts of dimethyl glutarate and 20 parts of dimethyl succinate were mixed with 30 parts of fine silica powder (trade name: Carplex #67, manufactured by Shionogi Pharmaceutical Co. Ltd.). Further, 5 parts of compound 1, 5 parts of a polyoxyethylene alkylaryl ether sulfate (trade name: Dikssol WK, manufactured by Daiichi Kogyoseiyaku) and 20 parts of clay were uniformly mixed thereto, followed by pulverization to obtain a wettable powder.

COMPARATIVE EXAMPLE 5

One part of compound 1, 79 parts of methylnaphthalene and 20 parts of a polyoxyethylene alkylaryl ether (trade name: Sorpol T-10, manufactured by Toho Chemical Co. Ltd.) were mixed and dissolved to obtain an emulsifierable concentrate.

COMPARATIVE EXAMPLE 6

Five parts of compound 10, 5 parts of a polyoxyethylene alkylaryl ether sulfate (trade name: Agrisol W-150S, manufactured by Kao), 12 parts of ethylene glycol, 0.1 part of xanthum gum and 77.9 parts of water were uniformly mixed, followed by pulverization to obtain a flowable.

COMPARATIVE EXAMPLE 7

Five parts of compound 23, 5 parts of fine silica powder (trade name: Carplex #80, manufactured by Shionogi Pharmaceutical Co. Ltd.), 5 parts of a polyoxyethylene alkylaryl ether sulfate (trade name: Dikssol WK, manufactured by Daiichi Kogyoseiyaku) and 85 parts of clay were uniformly mixed, followed by pulverization to obtain a wettable powder.

COMPARATIVE EXAMPLE 8

Five parts of compound 90, 5 parts of fine silica powder (trade name: Carplex #80, manufactured by Shionogi Pharmaceutical Co. Ltd.), 5 parts of a polyoxyethylenealkylarylether sulfate (trade name: Dikssol WK, manufactured by Daiichi Kogyoseiyaku) and 85 parts of clay were uniformly mixed, followed by pulverization to obtain a wettable powder.

COMPARATIVE EXAMPLE 9

Five parts of compound 96, 5 parts of fine silica powder (trade name: Carplex #80, manufactured by Shionogi Pharmaceutical Co. Ltd.), 5 parts of a polyoxyethylene alkylaryl ether sulfate (trade name: Dikssol WK, manufactured by Daiichi Kogyoseiyaku) and 85 parts of clay were uniformly mixed, followed by pulverization to obtain a wettable powder.

TEST EXAMPLE 1

Stability Test

The formulation prepared in each Example was put into a screw bottle made of glass and stored in a constant temperature container set at 50° C. for two weeks and under a room temperature condition for six months, whereupon it was analyzed by high performance liquid chromatography, and the remaining rate of the compound relative to the analytical value prior to the storage at 50° C., was determined. The results of the formulations prepared in accordance with Examples 1 to 9 and Comparative Example 1 to 9, are shown in Tables 13 and 14.

TABLE 13

| Test Examples | | Remaining rate (%) | |
|---|---|---|---|
| Formulation | Compound | Storage at 50° C. for 2 weeks | Storage at room temp. for 6 months |
| Example 1 | 131 | 99.8 | 99.9 |
| Example 2 | 131 | 99.7 | 100.0 |
| Example 3 | 131 | 99.9 | 99.7 |
| Example 4 | 131 | 99.8 | 99.8 |
| Example 5 | 131 | 98.8 | 99.1 |
| Example 6 | 132 | 98.6 | 99.3 |
| Example 7 | 133 | 99.5 | 99.4 |
| Example 8 | 134 | 98.9 | 99.6 |
| Example 9 | 135 | 99.2 | 99.4 |
| Comparative Example 1 | 131 | 55.3 | 72.8 |
| Comparative Example 2 | 131 | 63.4 | 77.1 |
| Comparative Example 3 | 131 | 58.4 | 82.6 |
| Comparative Example 4 | 131 | 70.1 | 85.5 |
| Comparative Example 5 | 131 | 47.8 | 50.2 |
| Comparative Example 6 | 132 | 72.2 | 80.0 |
| Comparative Example 7 | 133 | 62.7 | 69.5 |
| Comparative Example 8 | 134 | 65.0 | 71.5 |
| Comparative Example 9 | 135 | 53.3 | 66.3 |

TABLE 14

| Test Examples | | Remaining rate (%) | |
|---|---|---|---|
| Formulation | Compound | Storage at 50° C. for 2 weeks | Storage at room temp. for 6 months |
| Example 1 | 1 | 99.1 | 99.4 |
| Example 2 | 1 | 98.6 | 99.1 |
| Example 3 | 1 | 99.8 | 99.6 |
| Example 4 | 1 | 99.4 | 99.3 |
| Example 5 | 1 | 98.1 | 99.4 |
| Example 6 | 10 | 99.4 | 99.6 |
| Example 7 | 23 | 98.0 | 98.8 |
| Example 8 | 90 | 99.2 | 100.0 |
| Example 9 | 96 | 99.1 | 99.0 |
| Comparative Example 1 | 1 | 45.6 | 68.8 |
| Comparative Example 2 | 1 | 54.1 | 65.6 |
| Comparative Example 3 | 1 | 51.0 | 73.1 |
| Comparative Example 4 | 1 | 65.4 | 80.3 |
| Comparative Example 5 | 1 | 49.6 | 40.6 |
| Comparative Example 6 | 10 | 68.6 | 69.4 |
| Comparative Example 7 | 23 | 54.2 | 53.1 |
| Comparative Example 8 | 90 | 44.7 | 70.0 |
| Comparative Example 9 | 96 | 39.2 | 53.2 |

TEST EXAMPLE 2

Herbicidal Test

Upland soil was put into a plastic pot (surface area: 120 $cm_2$), and seeds of soybean, cocklebur (*Xanthium strumarium*), Slender amaranth (*Amaranthus viridis*), and Blue morningglory (*Ipomoea indica*) were sown and cultured at room temperature for 14 days. Then, a predetermined amount of the formulation prepared in accordance with each Example or Comparative Example and stored at room temperature or at 50° C. for a predetermined period, was diluted with water and sprayed to plants by a small size spraying machine for foliage treatment in an amount corresponding to 250 l/ha. After the treatment, the plants were cultured in a green house, and 21 days after the treatment, the herbicidal activities and phytotoxicity were examined on the basis of the following standards. The amounts of the active ingredients per hectare and the results of the herbicidal effects are shown in Tables 15 and 16.

INDEX

5: Completely withered
4: Herbicidal effects (phytotoxicity) of from 75% to 99%
3: Herbicidal effects (phytotoxicity) from 50% to 74%
2: Herbicidal effects (phytotoxicity) from 25% to 49%
1: Herbicidal effects (phytotoxicity) from 1% to 24%
0: No herbicidal effects (no phytotoxicity)

TABLE 15

| Test Examples Formulation | Compound | Dose g(a.i.)/ha | Herbicidal effects *1 | *2 | *3 | Phytotoxicity *4 |
|---|---|---|---|---|---|---|
| Example 1 | 1 | 10 | 5 | 5 | 4 | 0 |
|  |  | 5 | 4 | 5 | 4 | 0 |
| Example 1 (Stored at 50° C.) | 1 | 10 | 5 | 5 | 4 | 0 |
|  |  | 5 | 4 | 5 | 4 | 0 |
| Example 1 | 2 | 10 | 5 | 5 | 4 | 0 |
|  |  | 5 | 3 | 4 | 3 | 0 |
| Example 1 (Stored at 50° C.) | 2 | 10 | 5 | 5 | 4 | 0 |
|  |  | 5 | 4 | 4 | 3 | 0 |
| Example 1 | 3 | 10 | 5 | 5 | 5 | 0 |
|  |  | 5 | 4 | 5 | 4 | 0 |
| Example 1 (Stored at 50° C.) | 3 | 10 | 5 | 5 | 5 | 0 |
|  |  | 5 | 4 | 5 | 4 | 0 |
| Example 1 | 4 | 10 | 5 | 5 | 4 | 0 |
|  |  | 5 | 3 | 4 | 4 | 0 |
| Example 1 (Stored at 50° C.) | 4 | 10 | 5 | 5 | 4 | 0 |
|  |  | 5 | 3 | 4 | 4 | 0 |
| Example 1 | 5 | 10 | 5 | 5 | 4 | 0 |
|  |  | 5 | 4 | 4 | 3 | 0 |
| Example 1 (Stored at 50° C.) | 5 | 10 | 5 | 5 | 4 | 0 |
|  |  | 5 | 4 | 4 | 3 | 0 |
| Comparative Example 1 | 1 | 10 | 5 | 5 | 4 | 0 |
|  |  | 5 | 4 | 4 | 3 | 0 |
| Comparative Example 1 (Stored at 50° C.) | 1 | 10 | 3 | 4 | 3 | 1 |
|  |  | 5 | 2 | 2 | 1 | 0 |

*1 Cocklebur (Xanthium strumarium)
*2 Slender amaranth (Amaranthus viridis)
*3 Blue morningglory (Ipomoea india)
*4 Soybean

TABLE 16

| Test Examples Formulation | Compound | Dose g(a.i.)/ha | Herbicidal effects *1 | *2 | *3 | Phytotoxicity *4 |
|---|---|---|---|---|---|---|
| Example 1 | 131 | 10 | 5 | 4 | 4 | 0 |
|  |  | 5 | 5 | 3 | 3 | 0 |
| Example 1 (Stored at 50° C.) | 131 | 10 | 5 | 4 | 4 | 0 |
|  |  | 5 | 4 | 4 | 3 | 0 |
| Example 2 | 131 | 10 | 5 | 4 | 4 | 0 |
|  |  | 5 | 5 | 3 | 3 | 0 |
| Example 2 (Stored at 50° C.) | 131 | 10 | 5 | 4 | 4 | 0 |
|  |  | 5 | 5 | 3 | 3 | 0 |
| Example 3 | 131 | 10 | 5 | 4 | 4 | 0 |
|  |  | 5 | 4 | 3 | 3 | 0 |
| Example 3 (Stored at 50° C.) | 131 | 10 | 5 | 4 | 4 | 0 |
|  |  | 5 | 4 | 3 | 3 | 0 |
| Example 4 | 131 | 10 | 5 | 5 | 4 | 0 |
|  |  | 5 | 3 | 3 | 3 | 0 |
| Example 4 (Stored at 50° C.) | 131 | 10 | 5 | 5 | 4 | 0 |
|  |  | 5 | 3 | 3 | 3 | 0 |

TABLE 16-continued

| Test Examples Formulation | Compound | Dose g(a.i.)/ha | Herbicidal effects *1 | *2 | *3 | Phytotoxicity *4 |
|---|---|---|---|---|---|---|
| Comparative Example 1 | 131 | 10 | 5 | 4 | 4 | 0 |
|  |  | 5 | 4 | 3 | 3 | 0 |
| Comparative Example 1 (Stored at 50° C.) | 131 | 10 | 4 | 3 | 3 | 2 |
|  |  | 5 | 2 | 1 | 2 | 1 |
| Comparative Example 2 | 131 | 10 | 5 | 4 | 4 | 0 |
|  |  | 5 | 4 | 3 | 3 | 0 |
| Comparative Example 2 (Stored at 50° C.) | 131 | 10 | 4 | 3 | 3 | 2 |
|  |  | 5 | 3 | 1 | 1 | 1 |
| Comparative Example 3 | 131 | 10 | 4 | 4 | 4 | 0 |
|  |  | 5 | 3 | 2 | 3 | 0 |
| Comparative Example 3 (Stored at 50° C.) | 131 | 10 | 3 | 3 | 3 | 3 |
|  |  | 5 | 2 | 1 | 2 | 1 |
| Comparative Example 4 | 131 | 10 | 5 | 4 | 4 | 0 |
|  |  | 5 | 3 | 3 | 3 | 0 |
| Comparative Example 4 (Stored at 50° C.) | 131 | 10 | 3 | 2 | 3 | 3 |
|  |  | 5 | 2 | 2 | 2 | 2 |

*1 Cocklebur (Xanthium strumarium)
*2 Slender amaranth (Amaranthus viridis)
*3 Blue morningglory (Ipomoea india)
*4 Soybean

We claim:

1. A herbicidal composition, comprising a condensed heterocyclic compound of the formula:

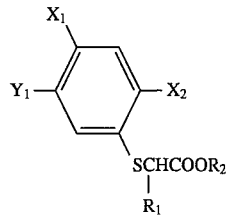

or

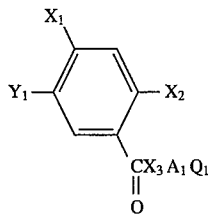

wherein each of $X_1$ and $X_2$ is hydrogen;

$R_1$ is hydrogen or halogen;

$R_2$ is hydrogen, alkyl, cycloalkyl or alkoxyalkyl;

$X_3$ is an oxygen atom or a sulfur atom;

$A_1$ is a linear or branched alkylene;

$Q_1$ is phenyl, halogen-substituted phenyl, cycloalkoxycarbonyl, alkylthio, alkoxycarbonyl, alkoxyalkoxycarbonyl, alkoxycarbonylalkylthio or alkylthioalkoxycarbonyl, and $Y_1$ is a group of the formula:

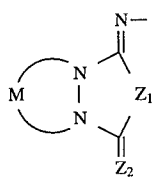

or

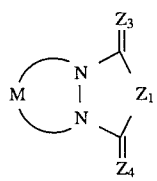

wherein each of $Z_1$, $Z_2$, $Z_3$ and $Z_4$ is an oxygen atom or a sulfur atom; and M is $C_4$-alkylene or C-alkenylene, and N-alkyl-2-pyrrolidone and another organic solvent,
and wherein sad another organic solvent is selected from the group consisting of a glycol, an alcohol, a vegetable oil, a mineral oil, an aromatic hydrocarbon, a fatty acid and an ester, and is present in an amount which increases the storage stability of the composition.

2. The herbicidal composition according to claim 1, wherein the organic solvent is an aromatic hydrocarbon solvent.

3. The herbicidal composition according to claim 2, wherein said aromatic hydrocarbon solvent is methylnaphthalene.

4. The herbicidal composition according to claim 1, wherein the condensed heterocyclic compound is of the formula:

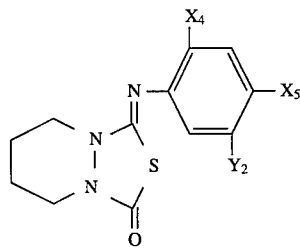

wherein each of $X_4$ and $X_5$ is a hydrogen atom or a halogen atom;

$Y_2$ is a group of the formula:

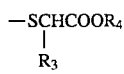

wherein $R_3$ is a hydrogen atom or alkyl;
$R_4$ is alkyl, cycloalkyl or alkoxyalkyl

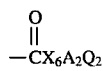

or a group of the formula:
wherein $X_6$ is an oxygen atom or a sulfur atom;
$A_2$ is linear or branched alkylene; and $Q_2$ is phenyl, halogen-substituted phenyl, cycloalkoxycarbonyl, alkylthio, alkoxycarbonyl, alkoxyalkoxycarbonyl, alkoxycarbonylalkythio or alkylthioalkoxycarbonyl.

5. The herbicidal composition according to claim 4 wherein $R_3$ is a hydrogen atom or lower alkyl; and $R_4$ is lower alkyl or cycloalkyl.

6. The herbicidal composition according to claim 1, wherein said N-alkyl-2-pyrrolidone is N-methyl-2-pyrrolidone and said organic solvent is methylnaphthalene.

7. The herbicidal composition according to claim 1, wherein the condensed heterocyclic compound is of the formula:

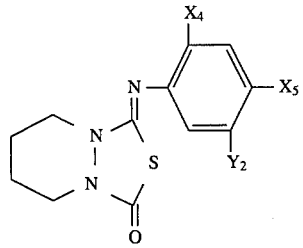

wherein $X_4$ and $X_5$ is a hydrogen atom or a halogen atom; and $Y_2$ is a group of the formula:

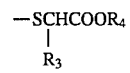

wherein $R_3$ is a hydrogen atom or an alkyl group; and
$R_4$ is alkyl, cycloalkyl, or alkoxyalkyl.

8. The herbicidal composition according to claim 1, wherein the ratio of the condensed heterocyclic compound to the N-alkyl-2-pyrrolidone is within a range of from 2:1 to 1:1,000.

9. The herbicidal composition according to claim 1, wherein said another organic solvent is a glycol selected from the group consisting of ethylene glycol, propylene glycol and polyethylene glycol.

10. The herbicidal composition according to claim 1, wherein said another organic solvent is an alcohol selected from the group consisting of methanol, n-propyl alcohol, isopropyl alcohol and isostearyl alcohol.

11. The herbicidal composition according to claim 1, wherein said another organic solvent is a vegetable oil selected from the group consisting of soybean oil and rapeseed oil.

12. The herbicidal composition according to claim 1 wherein said another organic solvent is a mineral oil selected from the group consisting of kerosene, spindle oil and liquid paraffin.

13. The herbicidal composition according to claim 1, wherein said another organic solvent is an aromatic hydrocarbon selected from the group consisting of methylnaphthalene and phenylxylylethane.

14. The herbicidal composition according to claim 1, wherein said another organic solvent is a fatty acid selected from the group consisting of oleic acid and isostearic acid.

15. The herbicidal composition according to claim 1, wherein said another organic solvent is an ester selected from the group consisting of tributyl phosphate, dioctyl phthalate, dimethyl glutarate and dimethyl succinate.

* * * * *

UNITED STATES PATENT AND TRADEMARK OFFICE
CERTIFICATE OF CORRECTION

PATENT NO. : 5,576,269
DATED : November 19, 1996
INVENTOR(S) : Yoshinori HIRABAYASHI, et al.

It is certified that error appears in the above-indentified patent and that said Letters Patent is hereby corrected as shown below:

On the title page, Item [63], the Related U.S. Application Data is printed incorrectly. It should read:

-- [63] Continuation of Ser. No. 185,965, filed as PCT/JP93/00955, Jul. 9, 1993, abandoned. --

Signed and Sealed this

Eighth Day of April, 1997

Attest:

BRUCE LEHMAN

*Attesting Officer*  *Commissioner of Patents and Trademarks*